(12) United States Patent
Yamashita

(10) Patent No.: US 8,774,489 B2
(45) Date of Patent: Jul. 8, 2014

(54) OPHTHALMOLOGY INFORMATION PROCESSING APPARATUS AND METHOD OF CONTROLLING THE SAME

(75) Inventor: Yutaka Yamashita, Shiroi (JP)

(73) Assignee: Canon Kabushiki Kaisha, Tokyo (JP)

( * ) Notice: Subject to any disclaimer, the term of this patent is extended or adjusted under 35 U.S.C. 154(b) by 118 days.

(21) Appl. No.: 13/407,970

(22) Filed: Feb. 29, 2012

(65) Prior Publication Data

US 2012/0237108 A1  Sep. 20, 2012

(30) Foreign Application Priority Data

Mar. 18, 2011  (JP) ................. 2011-060665

(51) Int. Cl.
*G06K 9/00* (2006.01)
(52) U.S. Cl.
USPC ........................................... 382/134
(58) Field of Classification Search
USPC ............. 348/234, 396.1, E5.035; 358/520; 382/134; 386/311, 312; 702/21
See application file for complete search history.

(56) References Cited

U.S. PATENT DOCUMENTS

| | | | |
|---|---|---|---|
| 2007/0216909 A1 | 9/2007 | Everett et al. | |
| 2008/0273174 A1 | 11/2008 | Tan | |
| 2009/0247998 A1* | 10/2009 | Watanabe et al. | 606/5 |

FOREIGN PATENT DOCUMENTS

| | | | | |
|---|---|---|---|---|
| CN | 1305354 A | 7/2001 | | |
| CN | 1589449 A | 3/2005 | | |
| EP | 604179 A2 * | 6/1994 | ............ | G01M 11/02 |
| JP | 2003-190096 A | 7/2003 | | |
| JP | 2007-029460 A | 2/2007 | | |
| JP | 2009-022506 A | 2/2009 | | |

OTHER PUBLICATIONS

Mar. 3, 2014 Chinese Official Action in Chinese Patent Appln. No. 201210070952.1.

* cited by examiner

*Primary Examiner* — Gregory F Cunningham
(74) *Attorney, Agent, or Firm* — Fitzpatrick, Cella, Harper & Scinto

(57) ABSTRACT

There is provided an ophthalmology information processing apparatus that allows to easily grasp a change in each part in continuously captured ophthalmology images. The ophthalmology information processing apparatus reads out a plurality of continuous captured images stored in a storage unit. An image analysis unit aligns the captured images. The ophthalmology information processing apparatus calculates the variation and position information of the pixel information of each pixel between the captured images based on the alignment information. An image generation unit generates a three-dimensional image which is displayed on a display unit simultaneously with the captured images.

13 Claims, 6 Drawing Sheets

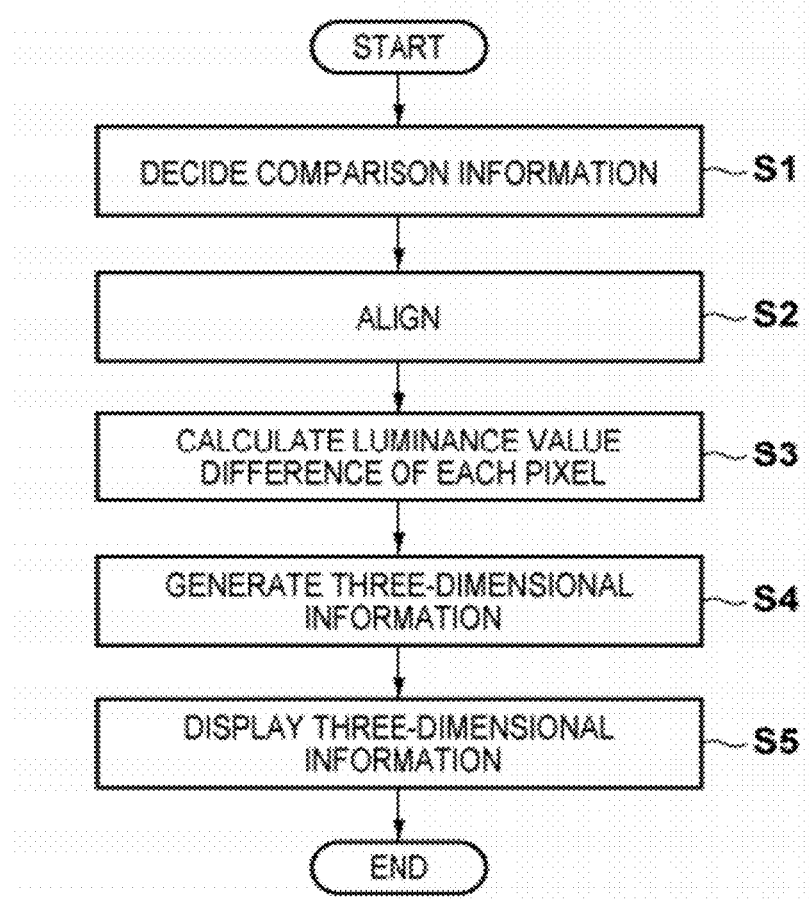

FIG. 4A
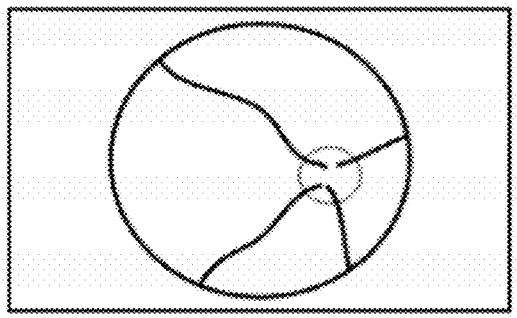
FIG. 4B
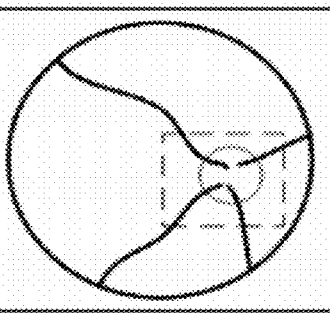
FIG. 5
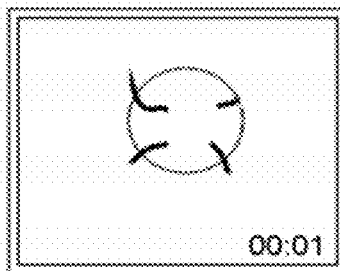 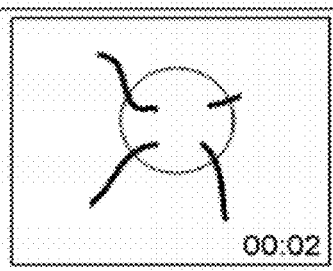 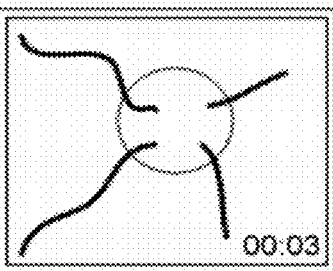

FIG. 6A
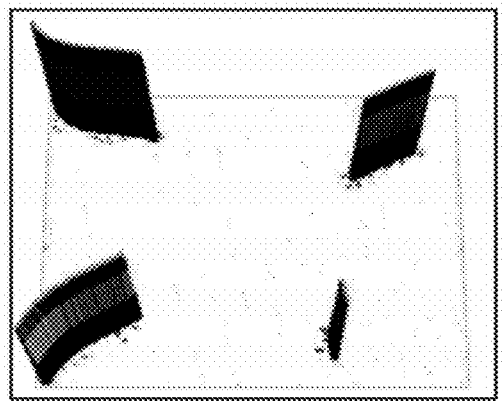
FIG. 6B
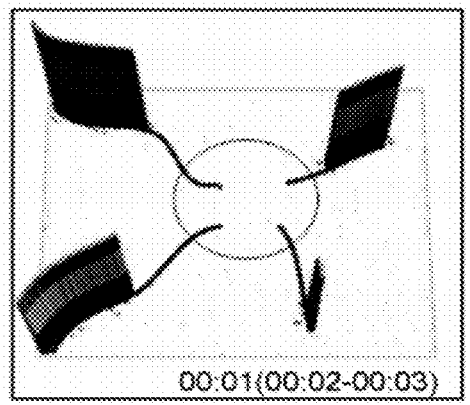
FIG. 7
| IMAGE UID | CAPTURED IMAGE UID | TIMER VALUE | THREE-DIMENSIONAL INFORMATION UID | COMPARISON TIME | MAXIMUM VARIATION |
|---|---|---|---|---|---|
| 3 | 1 | 00:02 | 15 | 1sec | 30 |
| 4 | 1 | 00:03 | 16 | 1sec | 26 |

OPHTHALMOLOGY INFORMATION PROCESSING APPARATUS AND METHOD OF CONTROLLING THE SAME

BACKGROUND OF THE INVENTION

1. Field of the Invention

The present invention relates to an ophthalmology information processing apparatus for processing an ophthalmology image captured by an ophthalmographic apparatus and a method of controlling the same.

2. Description of the Related Art

As an ophthalmographic apparatus, a fundus camera for capturing an image of the fundus of an eye to be examined is widely known. As the fundus camera, an apparatus that has a plurality of imaging modes such as color imaging, FAG (Fluorescent AngioGraphy), and ICG (IndoCyanin Green) angiography to perform imaging suitable for the examination purpose is known.

Fluorescent imaging such as FAG or ICG angiography is used to inspect the blood circulation state in the fundus blood vessels and find a morbid portion of the fundus by observing fluorescence leakage or hypofluorescence.

As an effective diagnostic method in the fluorescent imaging, fundus images after intravenous injection of a fluorescent agent are recorded as a moving image, and interpretation is done based on the recorded moving image.

Recently, widespread digital image filing systems allow to easily display captured images stored in a computer or a database. There also exist an apparatus for highlighting a designated portion of a captured image by image processing and an apparatus for displaying a three-dimensional image based on the luminance (light intensity) distribution information of the pixels of each captured image (Japanese Patent Laid-Open Nos. 2003-190096 and 2007-029460). Another system compares captured images during follow-up and displays change information concerning the images (Japanese Patent Laid-Open No. 2009-022506).

However, when observing a change in images obtained at a short time interval by, for example, moving image capturing, it is difficult to grasp the changing portion because the variation is very small in the three-dimensional display based on the absolute values of luminances. In addition, it is difficult to visually grasp a small change when the variation in the changing portion is represented by a color distribution on a plane.

SUMMARY OF THE INVENTION

The present invention has been made in consideration of the above-described problems, and provides an ophthalmology information processing apparatus that allows to easily grasp a small change in captured images, and a method of controlling the same.

According to one aspect of the present invention, an ophthalmology information processing apparatus for processing continuously captured ophthalmology images of a plurality of frames is provided. The apparatus includes a calculation unit configured to calculate a variation in a luminance value of each pixel between frames of the ophthalmology images of the plurality of frames, and a display unit configured to display a graph in which the variation is expressed as a three-dimensional height corresponding to the variation.

Further features of the present invention will become apparent from the following description of exemplary embodiments (with reference to the attached drawings).

BRIEF DESCRIPTION OF THE DRAWINGS

FIG. 3 is a flowchart showing the operation of the ophthalmology information processing apparatus according to the embodiment;

FIGS. 4A and 4B are views for explaining designation of a range to display the variation in captured images;

FIG. 5 is a view for explaining continuous images in which the range to display the variation in captured images is designated;

FIGS. 6A and 6B are views showing examples of three-dimensional display of the variation in captured images;

FIG. 7 is a table for explaining thumbnail information of three-dimensional information;

DESCRIPTION OF THE EMBODIMENTS

Various exemplary embodiments, features, and aspects of the invention will be described in detail below with reference to the drawings.

Figure 1:
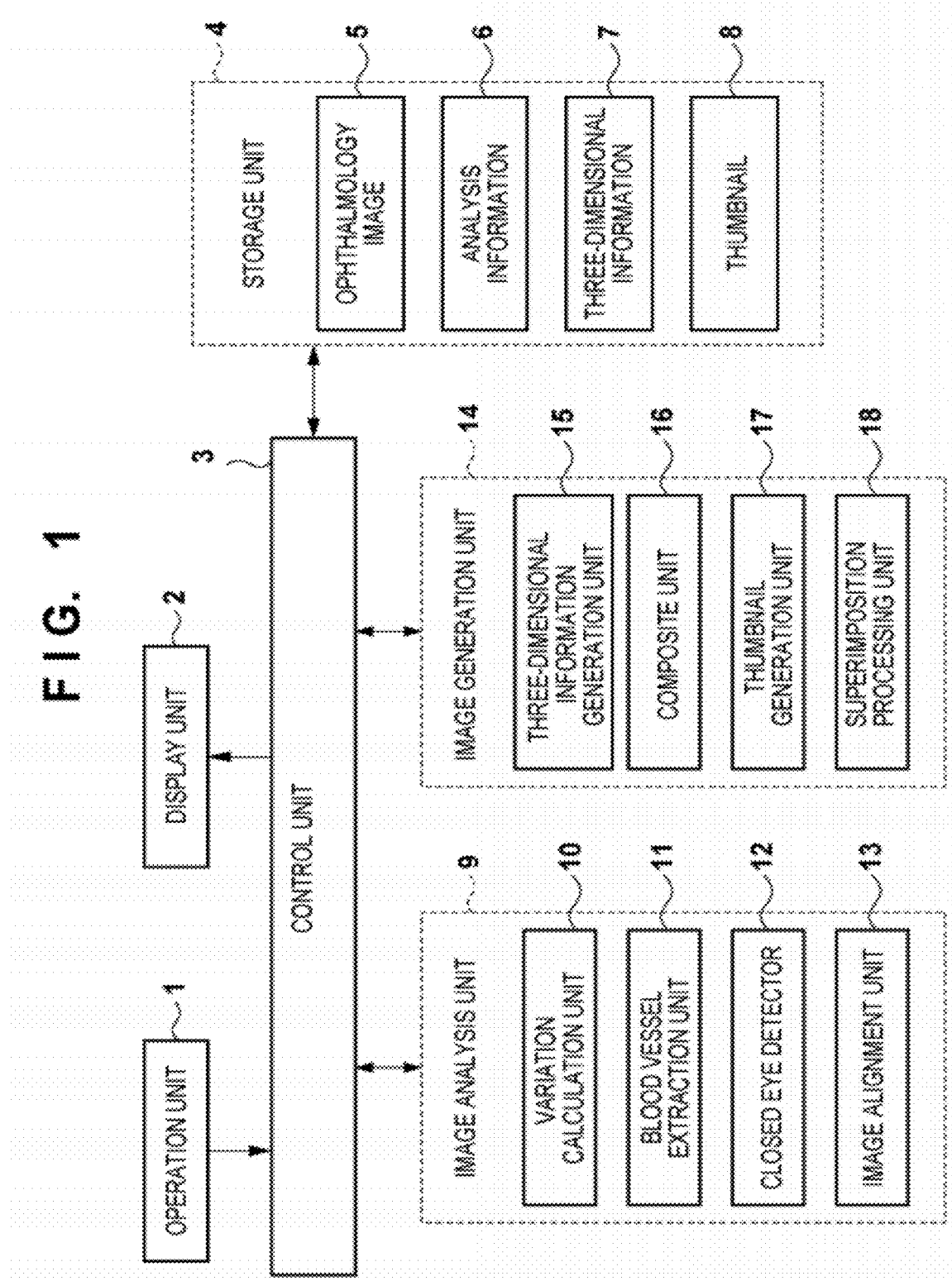
FIG. 1 is a block diagram showing the functional arrangement of an ophthalmology information processing apparatus according to an embodiment.

FIG. 1 is a block diagram showing the functional arrangement of an ophthalmology information processing apparatus according to the embodiment. This ophthalmology information processing apparatus includes a computer used by an operator. The computer is connected via a communication line such as a LAN (Local Area Network) to a database that stores and manages ophthalmology images, patient information, and the like. Note that the ophthalmology information processing apparatus may be formed from a single computer, and ophthalmology images and the like may be stored in an external storage device, for example, a CD (Compact Disc). The ophthalmology information processing apparatus may be connected to an ophthalmographic apparatus via a communication line. Examples of the ophthalmographic apparatus are a fundus camera and an SLO (Scanning Laser Ophthalmoscope).

As shown in FIG. 1, the ophthalmology information processing apparatus includes an operation unit 1, a display unit 2, a control unit 3, a storage unit 4, an image analysis unit 9, and an image generation unit 14.

The storage unit 4 will be described. The storage unit 4 stores an ophthalmology image 5, analysis information 6, three-dimensional information 7, and a thumbnail 8. The ophthalmology image 5 is an image of an eye to be examined acquired by the ophthalmographic apparatus. Examples are a single image captured by a fundus camera, continuously captured ophthalmology images of a plurality of frames, and a moving image thereof. Examples of the continuously captured ophthalmology images of a plurality of frames are a plurality of images continuously captured at a predetermined time interval in fluorescent fundus imaging and a moving image. Each ophthalmology image is stored together with additional information such as the part of the eye to be examined, the capturing date/time, and the elapsed time (timer value) of fluorescent angiography. The part of the eye to be examined includes left/right eye information and information of optic disc or macula.

The analysis information 6 is image analysis information created by the image analysis unit 9 and stored in the storage unit 4 by the control unit 3.

The three-dimensional information 7 is created by the image generation unit 14 and stored in the storage unit 4 by the control unit 3.

The thumbnail 8 is thumbnail information created by the image generation unit 14 and stored in the storage unit 4 by the control unit 3.

The ophthalmology image 5, the analysis information 6, the three-dimensional information 7, and the thumbnail 8 stored in the storage unit 4 are associated by the control unit 3, and the association information is stored in the storage unit 4. The association information may additionally include identification information representing the patient and part the ophthalmology image concerns.

The operation unit 1 includes arbitrary operation devices and input devices such as a keyboard, a mouse, a trackball, and a touch panel. The display unit 2 displays a screen and data in accordance with an instruction from the control unit 3. The display unit 2 is formed from an arbitrary display device such as an LCD (Liquid Crystal Display) or a CRT (Cathode Ray Tube). Also usable is a device formed by integrating the display unit with an operation unit such as a touch panel described as the operation unit 1. In this case, the operation unit and the display unit shown in FIG. 1 are integrated. The control unit 3 controls the units of the ophthalmology information processing apparatus.

The image analysis unit 9 includes an image alignment unit 13, a variation calculation unit 10, a blood vessel extraction unit 11, and a closed eye detector 12. The image alignment unit 13 calculates alignment information for aligning images between adjacent frames. The variation calculation unit 10 calculates the variation of the luminance value of each pixel from the aligned images and the image capturing time or timer information added to the images. The blood vessel extraction unit 11 extracts a blood vessel from an ophthalmology image. The closed eye detector 12 determines whether an ophthalmology image is an image where the eye is closed. The analysis information obtained by the image analysis unit 9 is stored in the storage unit 4 under the control of the control unit 3.

The image generation unit 14 includes a three-dimensional information generation unit 15, a composite unit 16, a thumbnail generation unit 17, and a superimposition processing unit 18. The three-dimensional information generation unit 15 generates three-dimensional information from the analysis information 6 stored in the storage unit 4. The composite unit 16 generates an image by compositing the ophthalmology image with the three-dimensional information. The thumbnail generation unit 17 generates a thumbnail image from the ophthalmology image, the three-dimensional information, and the composite image. The superimposition processing unit 18 superimposes the ophthalmology image on the image of the three-dimensional information. The image generated by the image generation unit 14 is displayed on the display unit 2 under the control of the control unit 3. The image generated by the image generation unit 14 is stored in the storage unit 4 under the control of the control unit 3.

Figure 2:
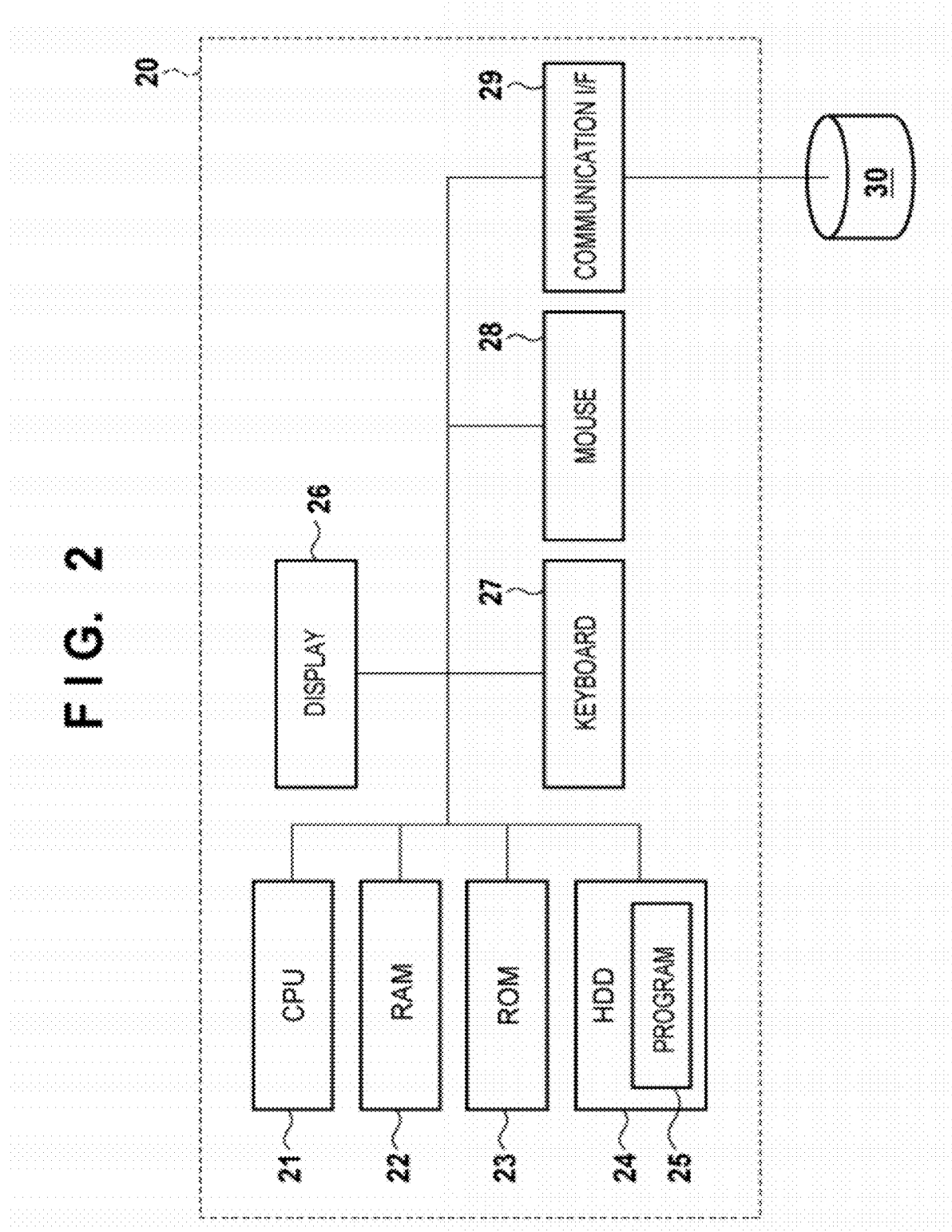
FIG. 2 is a block diagram showing the hardware arrangement of the ophthalmology information processing apparatus according to the embodiment.

FIG. 2 shows an example of the hardware arrangement of the ophthalmology information processing apparatus. The ophthalmology information processing apparatus includes a computer 20. A database 30 includes a server that stores and manages ophthalmology images, patient information, and the like. The computer 20 is connected to the database 30 via a communication line such as a LAN.

The operator inputs an ophthalmology image browsing request to the computer 20. The request is input by inputting or selecting patient identification information such as a patient name or a patient ID and performing a predetermined operation (for example, key input on the keyboard or mouse click). The computer 20 transmits the input request to the database 30. The database 30 searches for the ophthalmology image based on the request and transmits the image to the computer 20. The computer 20 displays the search result.

The computer 20 functions as, for example, the operation unit 1, the display unit 2, the control unit 3, the image analysis unit 9, and the image generation unit 14 shown in FIG. 1. The database 30 functions as the storage unit 4.

The computer 20 includes a CPU 21, a RAM 22 that functions as a main storage device, a ROM 23 that functions as an external storage device, and an HDD (Hard Disk Drive) 24 serving as an external storage device. The computer 20 also includes a display 26, a keyboard 27, a mouse 28, and a communication I/F 29. The CPU 21 expands, on the RAM 22, a program 25 stored in the HDD 24, thereby executing the operation of this embodiment.

FIG. 3 is a flowchart of displaying the three-dimensional information of a variation according to the embodiment. An example will be described here in which the ophthalmology image is a fundus image captured by a fundus camera. The display device of the display unit 2 is a display, and the operation unit 1 is implemented by a mouse and a keyboard.

In step S1, comparison information is decided. In this case, the operator can select a fundus image that should undergo variation calculation by operating the mouse. Image selection can be done either by selecting two still images or by selecting a moving image. The moving image selection may be done by selecting one moving image and setting time information concerning the comparison target. As the time information, for example, a frame or a timer interval (sec) can be set. Alternatively, a designated image and a reproduced moving image may be compared. As the designated image, a start image may be designated, or an image may be designated based on a timer value or the like.

When calculating the variation between the frames of a moving image, it is determined whether each frame of the selected moving image is an image where the eye is closed. The variation is calculated after each image where the eye is closed is removed. If the blood vessels of a fundus image are not included in the variation calculation, the blood vessels are extracted from the selected images, and the luminance value information of the blood vessel portions is set to a predetermined value such as "0". Note that a comparison range may be set for the fundus image at the time of image selection. For example, when the image shown in FIG. 4A is selected, the region of the comparison target can be selected by surrounding it by a broken line, as shown in FIG. 4B. In this case, the variation between the adjacent images is calculated for the continuous images at 00:01 to 00:03 in the designated range, as shown in FIG. 5.

When the comparison information decision processing of step S1 is completed, alignment processing of the images to be compared is performed (S2). Next, for the aligned images, the luminance value variation (difference) in each pixel between adjacent images is calculated (S3). For a color image, the variation may be calculated for each of the RGB components. When removing the blood vessels, the blood vessels are excluded from the variation calculation, or the calculation is done assuming that there is no variation.

Three-dimensional information is generated next by setting the luminance value variation of each pixel calculated in step S3 in the height direction (S4). At this time, the variation may be normalized by a predetermined luminance value. The generated three-dimensional information is displayed on the display unit 2 (S5). More specifically, a graph is displayed in which the variation is expressed as a three-dimensional height corresponding to the variation at the position of each pixel on two-dimensional coordinates where the ophthalmology image is displayed. Note that the luminance variation proves to be negative upon variation calculation, three-dimensional information may be displayed as a concave pattern. FIGS. 6A and 6B show examples of three-dimensional display. In FIG. 6A, the three-dimensional information is expressed as a color that changes in accordance with the variation. At this time, a representative image (for example, the image at 00:03 in FIG. 5) may be superimposed on the graph on the two-dimensional coordinates, as shown in FIG. 6B. Alternatively, a captured image may be superimposed on the surface of the three-dimensional information as a texture image. FIG. 6B shows an indication "00:01 (00:02-00:03)". This means that the original image is the image at 00:01, and the comparison target images are the images at 00:02 to 00:03.

Figure 8:
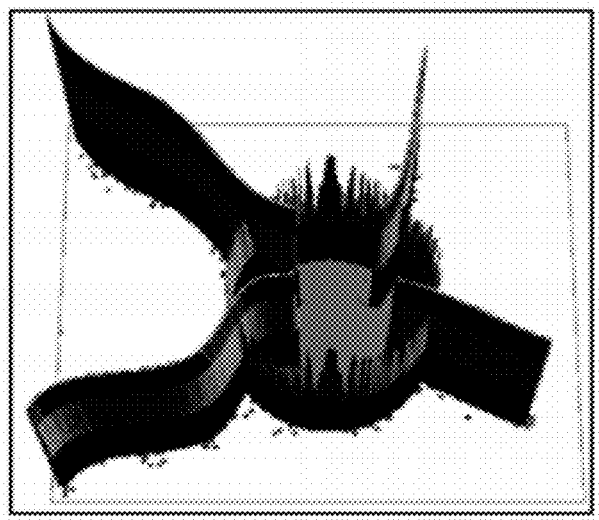
FIG. 8 is a view showing an example of three-dimensional display of the absolute values in captured images.
Figure 9:
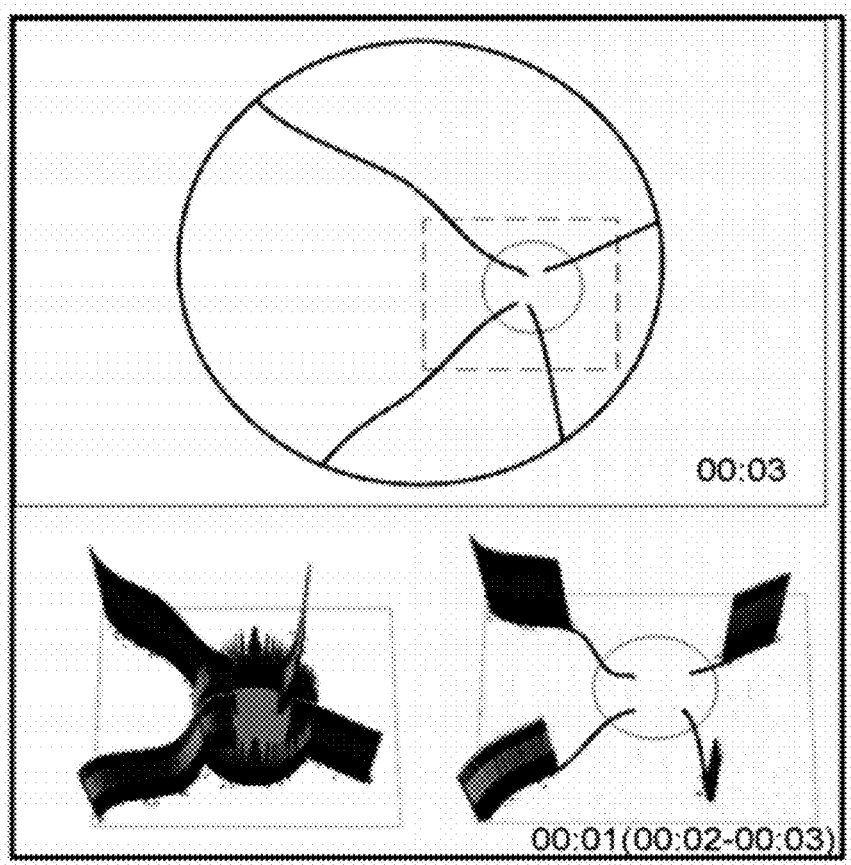
FIG. 9 is a view showing an example in which three-dimensional display of the variation in captured images, three-dimensional display of the absolute values in captured images, and a captured image are displayed simultaneously.

For a moving image, the maximum value of the variation in each pixel between the frames may be displayed. Alternatively, the three-dimensional information of the absolute values of luminances may be displayed, as shown in FIG. 8. Otherwise, the reproduced moving image, the three-dimensional information of the luminance variation as shown in FIG. 6B, and the three-dimensional information of the absolute values of luminances as shown in FIG. 8 may be displayed simultaneously, as shown in FIG. 9. The above-described maximum variation may also be displayed simultaneously. An image of the same part in another imaging mode, for example, a color image or a tomogram of OCT may be displayed in addition to the captured image. At this time, the alignable image of the same part can be displayed either in place of the captured image shown in FIG. 6B, or a mode may be provided in which the image or the captured image is selectively displayed.

Note that the calculated three-dimensional information is stored in the storage unit 4 by the control unit 3 that has received a storage instruction via the operation unit 1. When the variation of each pixel falls within a preset range, thumbnail information may be generated automatically and stored in the storage unit 4. The information stored as the thumbnail information includes, for example, the captured image UID of the target, a timer value and three-dimensional information UID for fluorescent imaging, an image comparison time for variation calculation, and the maximum variation within the comparison time, as shown in FIG. 7. Left/right eye information, the image capturing time, and the information of captured images to be displayed simultaneously may also be included as other information.

The function of the above-described embodiment can be implemented by causing the CPU 21 to execute the program 25. That is, the program 25 includes a program code for implementing the operation of the above-described embodiment. In other words, when the CPU 21 executes the program 25, the following functions are implemented.

(1) Continuous images to be three-dimensionally displayed are selected, the selected ophthalmology images are read out and aligned, and the luminance variation for the selected images is calculated.

(2) Three-dimensional information is generated from the luminance variation and displayed.

(3) The three-dimensional information is stored.

(4) A thumbnail image is generated, based on the luminance variation, for a designated luminance variation, and the generated thumbnail image is displayed and stored.

(5) The three-dimensional information and the ophthalmology image are superimposed and displayed.

(6) Maximum variation information that holds the maximum value of the luminance variation of each pixel is stored and displayed.

According to this program, the variation of continuously captured ophthalmology images of, for example, a moving image can be three-dimensionally displayed on the ophthalmology image. For this reason, a small variation can easily be confirmed as compared to the related art. This makes it possible to efficiently find a morbid portion of a fundus in fluorescent imaging and quantify the morbid portion.

In addition, according to this program, a thumbnail image can be stored for a designated variation. This facilitates grasping the portion and timing of change and the degree of change in continuous image capturing.

Furthermore, according to this program, the maximum value of the variation of each pixel can be stored. It is therefore possible to easily grasp whether the luminance has changed moderately or abruptly up to a predetermined luminance value from the start to the end of image capturing at the time of continuous image capturing.

Note that the program can be stored in an arbitrary storage medium readable by the drive of a computer. For example, a storage medium such as an optical disk, a magnetooptical disk (for example, CD-ROM, DVD-RAM, DVD-ROM, or MO), or a magnetic storage medium (for example, a hard disk or ZIP) is usable. The program can also be stored in a storage device such as a hard disk drive or a memory.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-060665, filed Mar. 18, 2011, which is hereby incorporated by reference herein in its entirety.

What is claimed is:

1. An ophthalmic information processing apparatus for processing continuously captured ophthalmic images of a plurality of frames, the apparatus comprising:

a calculation unit configured to calculate a variation in a luminance value of each pixel between frames of the ophthalmic images of the plurality of frames; and a display unit configured to display a graph in which the variation is expressed as a three-dimensional height corresponding to the variation.

2. The apparatus according to claim 1, wherein said display unit displays a representative image of the ophthalmic images of the plurality of frames on two-dimensional coordinates where the ophthalmic images are displayed, the representative image being superimposed on the graph.

3. The apparatus according to claim 1, further comprising a detection unit configured to detect an image where an eye is closed from the ophthalmic images of the plurality of frames,
wherein said calculation unit calculates the variation while excluding the image detected by said detection unit where the eye is closed.

4. The apparatus according to claim 1, wherein the graph is displayed in a color that changes in accordance with the variation.

5. The apparatus according to claim 2, further comprising an extraction unit configured to extract an image of a blood vessel region from the representative image,
wherein said display unit displays, in a predetermined color, the image of the blood vessel region extracted by said extraction unit.

6. The apparatus according to claim 1, wherein said display unit further displays a maximum value of the variation in the ophthalmic images of the plurality of frames.

7. A method of controlling an ophthalmic information processing apparatus for processing continuously captured ophthalmic images of a plurality of frames, the method comprising the steps of:
calculating a variation in a luminance value of each pixel between frames of the ophthalmic images of the plurality of frames; and
displaying a graph in which the variation is expressed as a three-dimensional height corresponding to the variation.

8. A computer-readable storage medium storing a program for controlling an ophthalmic information processing apparatus including a computer executing the program, the program comprising code for performing a method including the steps of:
calculating a variation in a luminance value of each pixel between frames of the ophthalmic images of the plurality of frames; and
displaying a graph in which the variation is expressed as a three-dimensional height corresponding to the variation.

9. An ophthalmic information processing apparatus for processing a first ophthalmic image and a second ophthalmic image, the apparatus comprising:
a calculation unit configured to calculate a variation in a luminance value of each pixel between the first ophthalmic image and the second ophthalmic image; and
a display unit configured to display a graph in which the variation is expressed as a three-dimensional height corresponding to the variation.

10. The apparatus according to claim 9, wherein said display unit displays the first ophthalmic image on two-dimensional coordinates, and
wherein the graph is superimposed on the first ophthalmic image.

11. The apparatus according to claim 9, wherein the graph is displayed in a color that changes in accordance with the variation.

12. The apparatus according to claim 10, further comprising an extraction unit configured to extract an image of a blood vessel region from the first ophthalmic image,
wherein said display unit displays, in a predetermined color, the image of the blood vessel region extracted by said extraction unit.

13. The apparatus according to claim 9, wherein said display unit further displays a maximum value of the variation in the first ophthalmic image and the second ophthalmic image.

* * * * *